US011583222B2

(12) United States Patent
Sartor et al.

(10) Patent No.: US 11,583,222 B2
(45) Date of Patent: Feb. 21, 2023

(54) SYSTEMS, DEVICES, AND METHODS FOR LYMPH SPECIMEN TRACKING, DRAINAGE DETERMINATION, VISUALIZATION, AND TREATMENT

(71) Applicant: COVIDIEN LP, Mansfield, MA (US)

(72) Inventors: Joe D. Sartor, Longmont, CO (US); Francesca Rossetto, Longmont, CO (US)

(73) Assignee: Covidien LP, Mansfield, MA (US)

(*) Notice: Subject to any disclaimer, the term of this patent is extended or adjusted under 35 U.S.C. 154(b) by 894 days.

(21) Appl. No.: 15/924,888

(22) Filed: Mar. 19, 2018

(65) Prior Publication Data

US 2018/0333095 A1 Nov. 22, 2018

Related U.S. Application Data

(60) Provisional application No. 62/508,724, filed on May 19, 2017.

(51) Int. Cl.
*A61B 5/00* (2006.01)
*G06T 7/33* (2017.01)
(Continued)

(52) U.S. Cl.
CPC .............. *A61B 5/418* (2013.01); *A61B 34/20* (2016.02); *A61B 34/25* (2016.02); *G06T 7/344* (2017.01);
(Continued)

(58) Field of Classification Search
CPC ........... A61B 5/418; A61B 5/414; A61B 5/41; A61B 34/20; A61B 34/25;
(Continued)

(56) References Cited

U.S. PATENT DOCUMENTS 6,188,355 B1    2/2001  Gilboa
6,810,281 B2   10/2004  Brock et al.
(Continued)

FOREIGN PATENT DOCUMENTS

CN    101167662 A    4/2008
CN    103839048 A    6/2014
(Continued)

OTHER PUBLICATIONS

U.S. Appl. No. 62/315,773, filed Mar. 31, 2016, by Sartor et al.
(Continued)

*Primary Examiner* — Ryan N Henderson
*Assistant Examiner* — Pamela F Wu
(74) *Attorney, Agent, or Firm* — Carter, DeLuca & Farrell LLP (57) ABSTRACT

Disclosed are systems and methods of lymphatic specimen tracking, visualization, and lymph node drainage pathway determination. An exemplary method includes receiving computed tomographic (CT) image data corresponding to a CT scan, generating a three-dimensional (3D) model of at least a portion of a patient's body based on the CT image data, identifying one or more lymph nodes in the 3D model, performing a registration of the 3D model with one or more physical locations in the patient's body, determining an expected lymph node drainage pathway away from a region of interest through one or more lymph nodes, and displaying the 3D model and the expected lymph node drainage pathway.

17 Claims, 7 Drawing Sheets

(51) Int. Cl.

| | | |
|---|---|---|
| *G06T 7/70* | (2017.01) | |
| *A61B 34/00* | (2016.01) | |
| *A61B 34/20* | (2016.01) | |
| A61B 10/00 | (2006.01) | |
| A61B 34/10 | (2016.01) | |
| A61B 90/00 | (2016.01) | |

(52) U.S. Cl.
CPC ............ *G06T 7/70* (2017.01); *A61B 10/0096* (2013.01); *A61B 90/361* (2016.02); *A61B 2034/105* (2016.02); *A61B 2034/2051* (2016.02); *A61B 2034/2072* (2016.02); *A61B 2034/252* (2016.02); *A61B 2034/254* (2016.02); *A61B 2090/392* (2016.02); *A61B 2090/395* (2016.02); *A61B 2090/3908* (2016.02); *A61B 2090/3933* (2016.02); *G06T 2207/10081* (2013.01)

(58) Field of Classification Search
CPC .... A61B 2034/2051; A61B 2034/2053; A61B 2034/2055; A61B 2034/252; A61B 2034/254; A61B 2034/256; A61B 2034/258; A61B 2034/2072; A61B 2090/3908; A61B 2090/3904; A61B 2090/392; A61B 2090/3933; A61B 2090/395; G06T 7/344; G06T 7/30; G06T 7/70; G06T 7/55; G06T 7/73; G06T 2207/10081
USPC ........................................................ 600/109
See application file for complete search history.

(56) References Cited

U.S. PATENT DOCUMENTS

| | | | | |
|---|---|---|---|---|
| 2002/0037252 A1* | 3/2002 | Toida | ................ | G01B 9/02003 424/9.6 |
| 2004/0162479 A1* | 8/2004 | Yamamoto | ............. | A61B 5/00 600/411 |
| 2011/0071403 A1* | 3/2011 | Sevick-Muraca | ...... | A61B 5/415 600/476 |
| 2011/0085720 A1 | 4/2011 | Averbuch | | |
| 2011/0118575 A1* | 5/2011 | Lloyd | ................. | A61B 5/0091 600/328 |
| 2012/0107831 A1* | 5/2012 | Hikage | ................. | B82Y 15/00 435/7.1 |
| 2016/0000414 A1* | 1/2016 | Brown | ..................... | A61B 6/50 600/567 |
| 2016/0166336 A1* | 6/2016 | Razzaque | ............. | A61B 34/25 606/130 |

FOREIGN PATENT DOCUMENTS

| | | |
|---|---|---|
| CN | 104000655 A | 8/2014 |
| CN | 106659373 A | 5/2017 |
| WO | 0010456 A1 | 3/2000 |
| WO | 0167035 A1 | 9/2001 |
| WO | 2013134559 A1 | 9/2013 |

OTHER PUBLICATIONS

U.S. Appl. No. 62/369,986, filed Aug. 2, 2016, by William S. Krimsky.

Takayuki Kitasaka, et al.: "Automated Extraction of Lymph Nodes from 3-D Abdominal CT Images Using 3-D Minimum Directional Difference Filter"; MICCAI 2007, Part II, LNCS 4792, pp. 336-343, 2007. Springer-Verlag Berline Heidelberg, 2007.

Philipp J. Stolka, et al.: "A 3D-elastography-guided system for laparoscopic partial nephrectomies", Proceedings of SPIE, vol. 7625, Mar. 4, 2010, p. 76251I-1.

Extended European Search Report issued in European Patent Application No. 18173137.3, dated Oct. 15, 2018 (10 pages).

Office Action issued in corresponding Chinese Appl. No. 201810478893.9 dated May 7, 2020 (10 pages).

European Examination Report issued in corresponding application EP 18173137.3 dated Jun. 11, 2021 (4 pages).

* cited by examiner

SYSTEMS, DEVICES, AND METHODS FOR LYMPH SPECIMEN TRACKING, DRAINAGE DETERMINATION, VISUALIZATION, AND TREATMENT

CROSS REFERENCE TO RELATED APPLICATION

The present application claims the benefit of and priority to U.S. Provisional Application Ser. No. 62/508,724, filed on May 19, 2017 the entire contents of which are incorporated herein by reference.

BACKGROUND

Technical Field

The present disclosure relates to systems, devices, and methods for lymph specimen drainage determination, tracking, visualization, treatment, and removal within the lymphatic system.

Description of Related Art

The lymphatic system is part of the circulatory system and is made of a network of lymphatic vessels or ducts that are designed to carry lymph to local lymph nodes throughout the body where the fluid is filtered, processed, and sent to the next lymph node down the line until the fluid reaches the thoracic duct or right lymphatic duct where it enters the blood stream. Lymph vessels infiltrate all tissues and organs of the body. Lymph is generated from capillaries which, because of tissue motion and hydrostatic pressure, enter the lymph vessels carrying with it local and foreign substances and materials from the tissues. In this regard, lymph nodes process fluid by sieving and phagocytosis to remove particulate and cell material delivered by the lymphatic vessels, thereby cleaning it before it is returned to the blood stream.

During procedures involving the treatment and/or removal of tumors and other cancerous tissue located, in particular, in and around the lung, it may be useful to determine the pathways of lymph drainage in order to determine potential movement of benign or malignant materials as it is filtered through the lymph nodes. While there are methods for tracking the pathways of the lymphatic system, there is always a need for improvement. The present disclosure provides for improved lymphatic specimen tracking, drainage pathway determination, visualization, and treatment of lymph nodes.

SUMMARY

Provided in accordance with embodiments of the present disclosure are methods of lymphatic specimen tracking, visualization, and lymph node drainage pathway determination. According to an aspect of the present disclosure, an exemplary method includes receiving computed tomographic (CT) image data corresponding to a CT scan, generating a three-dimensional (3D) model of at least a portion of a patient's body based on the CT image data, identifying one or more lymph nodes in the 3D model, performing a registration of the 3D model with one or more physical locations in the patient's body, determining an expected lymph node drainage pathway away from a region of interest through one or more lymph nodes, and displaying the 3D model and the expected lymph node drainage pathway.

In another aspect of the present disclosure, identifying one or more lymph nodes in the 3D model includes identifying drainage tiers of the one of more lymph nodes, and the drainage tiers are sentinel nodes, one or more secondary nodes, and/or one or more tertiary nodes.

In a further aspect of the present disclosure, identifying drainage tiers of the one of more lymph nodes includes color-coding the one or more lymph nodes based on a drainage tier corresponding to the one or more lymph nodes.

In another aspect of the present disclosure, the method further includes injecting the region of interest with a marking agent, sampling the one of more lymph nodes based on the expected lymph node drainage pathway, and measuring the marking agent within the one or more lymph nodes.

In a further aspect of the present disclosure, the marking agent is selected from the group consisting of an optical coloring agent and a radioactive tracer.

In another aspect of the present disclosure, the method further includes determining a measured lymph node drainage pathway away from the region of interest through the one or more lymph nodes based on the marking agent measured within the one or more lymph nodes, and displaying the measured lymph node drainage pathway.

In yet another aspect of the present disclosure, the marking agent is a radioactive agent and the displaying of the measured lymph node drainage pathway includes displaying measured emissions of the marking agent.

In still another aspect of the present disclosure, the method further includes generating lymph node information data based the one or more lymph nodes, and the lymph node information data includes one or more of drainage tiers, lymph node name, procedure type, patient information, date, marking agent measured, and clinician information.

In a further aspect of the present disclosure, the method further includes outputting the lymph node information data.

In another aspect of the present disclosure, the method further includes navigating a surgical instrument to the one of more lymph nodes, determining a location of the surgical instrument, analyzing the one or more lymph nodes at the location of the surgical instrument, and outputting the lymph node information data for the one or more lymph nodes at the location of the surgical instrument.

Provided in accordance with embodiments of the present disclosure are systems for lymphatic specimen tracking and visualization. According to an aspect of the present disclosure, an exemplary system includes a laparoscopic camera insertable into a patient and configured to obtain images, a surgical tool insertable into the patient, a camera sensor operatively associated with the laparoscopic camera, a tool sensor operatively associated with the surgical tool, an electromagnetic tracking system configured to track the camera sensor and the tool sensor, one or more processors configured to execute instructions which, when executed, cause the one or more processors to receive computed tomographic (CT) image data corresponding to a CT scan, generate a three-dimensional (3D) model of at least a portion of a patient's body from the CT image data, identify one or more lymph nodes inside the 3D model, perform a registration of the 3D model with one or more physical locations in the patient's body, and determine an expected lymph node drainage pathway away from a region of interest through one or more lymph nodes. The system further includes a display configured to display a user interface including the 3D model, the expected lymph node drainage pathway, and lymph node information data.

In another aspect of the present disclosure, the instructions, when executed, further cause the one or more processors to generate the user interface, the user interface including a sampling window configured to display the identified one or more lymph nodes and the surgical tool as it interacts with the identified one or more lymph nodes inside the patient's body.

In a further aspect of the present disclosure, the instructions, when executed, further cause the one or more processors to generate the user interface, the user interface including a measured drainage window configured to display the lymph node drainage pathway and lymph node information data.

In another aspect of the present disclosure, the instructions, when executed, further cause the one or more processors to generate the user interface, the user interface including a procedure window configured to display and track the surgical procedure being performed.

In yet another aspect of the present disclosure, the instructions, when executed, further cause the one or more processors to receive a previous 3D model of at least a portion of the patient's body including previous lymph node information data, and update the 3D model and lymph node information data based on the previous 3D model and previous lymph node information data.

In still another aspect of the present disclosure, the instructions, when executed, further cause the one or more processors to generate the user interface, the user interface including a removal window configured to display and update the lymph node information data during the surgical procedure.

In yet another aspect of the present disclosure, the instructions, when executed, further cause the one or more processors to identify drainage tiers of the one of more lymph nodes, wherein the drainage tiers are sentinel nodes and one or more secondary nodes.

In still another aspect of the present disclosure, the lymph node information data includes one or more of drainage tiers, lymph node name, patient information, date, and clinician information.

In yet another aspect of the present disclosure, the instructions, when executed, further cause the one or more processors to update the lymph node information data for the one or more lymph nodes as surgical tool interacts with the one or more lymph nodes.

In still another aspect of the present disclosure, the instructions, when executed, further cause the one or more processors to generate the user interface, the user interface including a location window configured to display a portion of the 3D model which corresponds with the images obtained by the laparoscopic camera.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure is directed to lymphatic specimen tracking, drainage pathway determination, visualization, and treatment of tumors or other regions of interest within the lymphatic system. During treatment of a tumor or other targets or regions of interest within the lung, it is necessary to ensure that all lymph nodes relevant to a treated or resected tumor are analyzed or removed. In order to determine that relevant lymph nodes are analyzed and/or removed, to ensure removal of biological material that may have moved throughout the body, it is necessary to accurately identify the relevant lymph nodes and the drainage pathways that stem from a tumor or region of interest.

Although this disclosure relates more particularly to the lymphatic system of the lungs and surround areas, in some embodiments, the systems and methods of the present disclosure may be used for various other forms of surgery, including abdominal surgery, joint surgery, etc. Further details about systems, devices, and methods for obtaining image data for and creation of a 3D model are provided in commonly-owned U.S. Provisional Patent Application No. 62/315,773, entitled "THORACIC ENDOSCOPE FOR SURFACE SCANNING," filed on Mar. 31, 2016, by Sartor et al., and commonly-owned U.S. Provisional Patent Application No. 62/369,986, entitled "SYSTEM AND METHOD OF USING AN ENDOSCOPIC CATHETER AS A PORT IN LAPAROSCOPIC SURGERY," filed on Aug. 2, 2016, by William S. Krimsky, the entire contents of both of which are incorporated herein by reference.

The systems, devices, methods, and computer-readable media described herein are useful for treatment procedures performed on the patient's lungs and surrounding tissue, as well as other areas of the patient's body. For example, in an embodiment where a clinician is performing treatment of an area of the patient's lungs, the methods and systems may provide the clinician with various views, including live images from one or more laparoscopes, one or more views of a 3D model, and one or more medical images, such as computed tomography (CT) or fluoroscopic images, obtained preoperatively or intra-operatively and selected for display based on the tracked location and direction of movement of a surgical tool used during the procedure. These and other aspects of the present disclosure are detailed hereinbelow.

Figure 1:
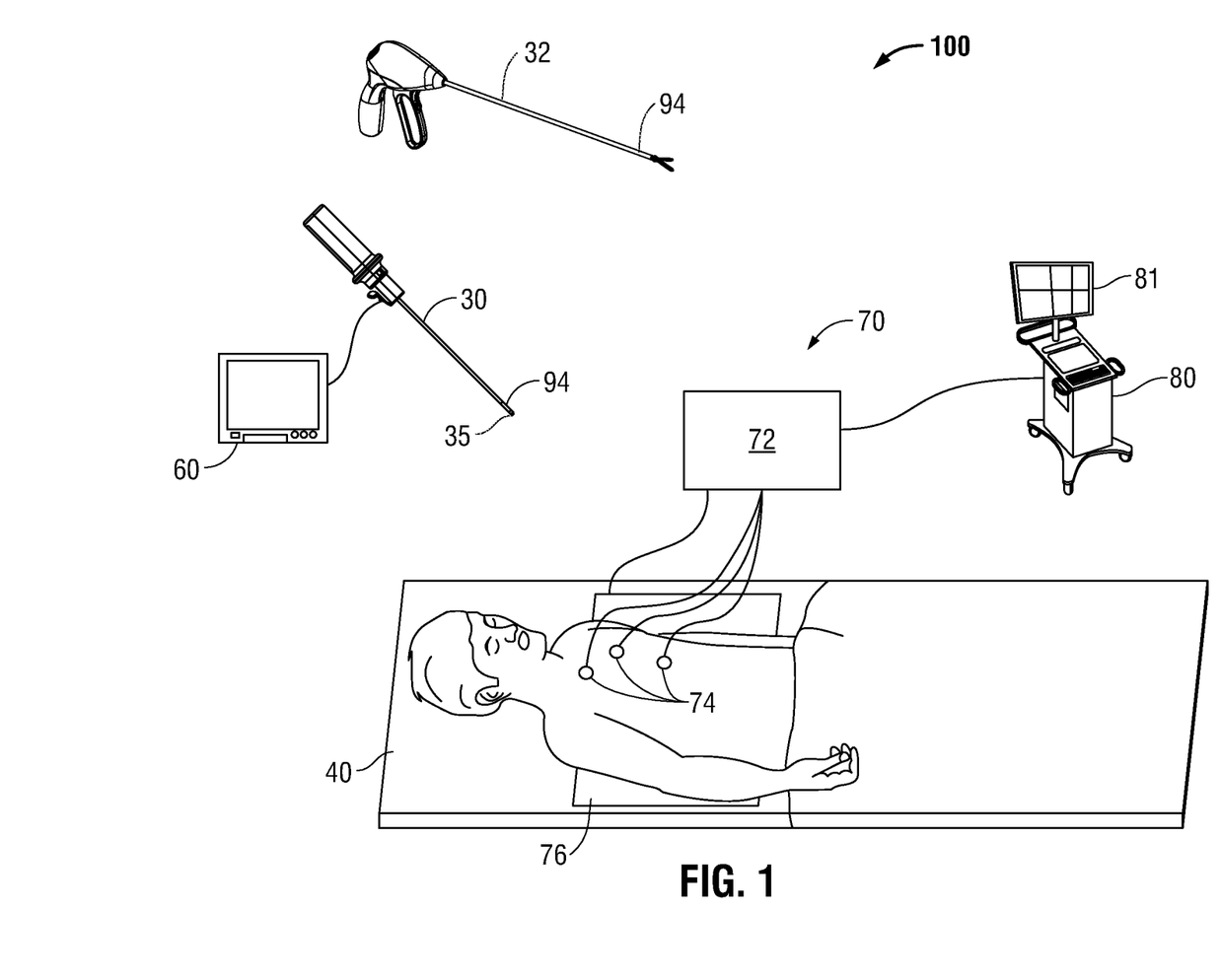
FIG. 1 illustrates a system suitable for performing laparoscopic surgery on a patient, in accordance with the present disclosure.

With reference to FIG. 1, a system 100 suitable for performing laparoscopic surgery on a patient is provided in accordance with an embodiment of the present disclosure. As shown in FIG. 1, system 100 is used to perform one or more treatment procedures on a patient supported on an operating table 40. In this regard, system 100 generally includes at least one laparoscope 30, at least one surgical tool 32, monitoring equipment 60, an electromagnetic (EM) tracking system 70, and a computing device 80.

Laparoscope 30 includes a source of illumination and a laparoscopic camera 35 coupled to monitoring equipment 60, for example, a video display, for displaying the video images received from camera 35. Laparoscope 30 is configured for insertion into the patient's body, e.g. through a surgical incision or a laparoscopic port, to provide images of a surgical site inside the patient's body, for example, inside the patient's thoracic cavity. As illustrated in FIG. 1, the patient is shown laying on operating table 40 with laparoscope 30 and surgical tool 32 nearby for insertion into the patient's body. Though depicted as an electrosurgical vessel sealer, surgical tool 32 may be any one of a number of surgical tools usable during laparoscopic surgery, including cutting tools, suction tools, single fine-needle aspiration tools, tracer injection tools, radiological detection tools, biopsy tools, resection tools, graspers, ablation tools, ligation tools, surgical staplers, ultrasonic and/or electrosurgical vessel sealers, etc.

EM tracking system 70 may be a six degrees-of-freedom EM tracking system, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR," filed on Dec. 14, 1998 by Gilboa, the entire contents of each of which are incorporated herein by reference, or any other suitable positioning measuring system, is utilized for performing tracking, although other configurations are also contemplated.

EM tracking system 70 may be configured for use with laparoscope 30 to track the position of EM sensor 94 as it moves in conjunction with laparoscope 30 about the patient's body, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the patient's chest. The six degrees of freedom coordinates of reference sensors 74 are sent as data to computing device 80, which includes an application, where the data from sensors 74 are used to calculate a patient coordinate frame of reference.

As such, laparoscope 30 further includes at least one EM sensor 94. The location of EM sensor 94, and thus the distal end of laparoscope 30, within an EM field generated by EM field generator 76 can be derived by tracking module 72, and computing device 80. Surgical tool 32 may also include one or more EM sensors 94 to be tracked by tracking module 72 similar to laparoscope 30.

Computing device 80 includes various software and/or hardware components, including one or more applications producing a graphic user interface for presentation on a display 81 as depicted in FIG. 1. Computing device 80 may include memory, one or more processors, a network interface, an input device, and/or an output module. The memory may store the applications and/or image data.

The network interface may be configured to connect to a network such as a local area network (LAN) consisting of a wired network and/or a wireless network, a wide area network (WAN), a wireless mobile network, a Bluetooth network, and/or the internet. The input device may be any device by means of which a user may interact with computing device 80, such as, for example, a mouse, keyboard, foot pedal, touch screen, and/or voice interface. The output module may include any connectivity port or bus, such as, for example, parallel ports, serial ports, universal serial busses (USB), or any other similar connectivity port known to those skilled in the art.

An application may be employed to facilitate the various phases of the treatment procedure, including generating the aforementioned 3D model, and navigating laparoscope 30 and/or surgical tool 32 to the treatment location. For example, computing device 80 utilizes CT scan, magnetic resonance imaging (MRI) scan, and/or positron emission tomography (PET) scan image data for generating and viewing the 3D model of the patient's airways. The CT scan generates two-dimensional (2D) slices of the patient's scanned region, which, for the example of the lungs, may include, among other things, airways, lesions, blood vessels, vascular structures, lymphatic vessels including lymph nodes, organs, and other physiological structures. By combining the slices, the model of the patient's airway tree, including the above-mentioned structures may, be generated. While the CT scan image data may have gaps, omissions, and/or other imperfections included in the image data, the 3D model and/or deflated 3D model is a smooth representation of the patient's airways, with any such gaps, omissions, and/or imperfections in the CT scan image data filled in or corrected. By combining all 2D slices, computing device 80 is able to generate the smoothed 3D model. The 3D model may be presented on a display 81 associated with computing device 80, or in any other suitable fashion.

Using computing device 80, various views of the 3D model may be presented and may be manipulated by a clinician to give the clinician a preferred view of the treatment location. The 3D model may include, among other things, a model airway tree corresponding to the actual airways of the patient's lungs showing the various passages, branches, and bifurcations of the patient's airway tree. Additionally, the 3D model may include lesions, markers, blood vessels and vascular structures, lymphatic vessels and structures, organs, other physiological structures such as the pleura and fissures of the lungs. Some or all of the aforementioned elements may be selectively displayed, such that the clinician may choose which elements should be displayed when viewing the 3D model. The 3D model may also be rotated and zoomed as necessary to achieve a desired view. Further, in accordance aspects described hereinbelow, a viewing angle may be keyed to a sensed location of laparoscope 30 and EM sensor 94, such that the view from the laparoscope can be seamlessly overlaid on the 3D model.

After generating the 3D model, a procedure may be undertaken in which tracking system 70 enables tracking of EM sensor 94 (and thus the distal end of laparoscope 30) as EM sensor 94 is positioned inside the patient's body. As an initial step of the procedure, the 3D model is registered with the patient's body. One potential method of registration involves navigating EM sensor 94 about the patient's body to identify various landmarks that may then be used to align the position of those landmarks in the 3D model with the position in the patient's body. The position of EM sensor 94 is tracked during this registration phase, and the 3D model is iteratively updated based on the tracked position of EM sensor 94 within the patient's body. Various other registration processes may also be used to register the 3D model with the patient's body. Examples of such registration processes are described in commonly-owned U.S. Patent Application Publication No. 2011/0085720, entitled "AUTO- MATIC REGISTRATION TECHNIQUE," filed on May 14, 2010, by Barak et al., the entire contents of which are incorporated herein by reference. While the registration process focuses on aligning the patient's body with the 3D model, registration also ensures that the position of airways, vascular structures, pleura, and fissures of the lungs are accurately determined. As will be appreciated, this registration enables the depiction of the sensed location of the EM sensor 94 associated with the laparoscope 30 or the surgical tool 32 accurately with respect to the 3D model.

Figure 2:
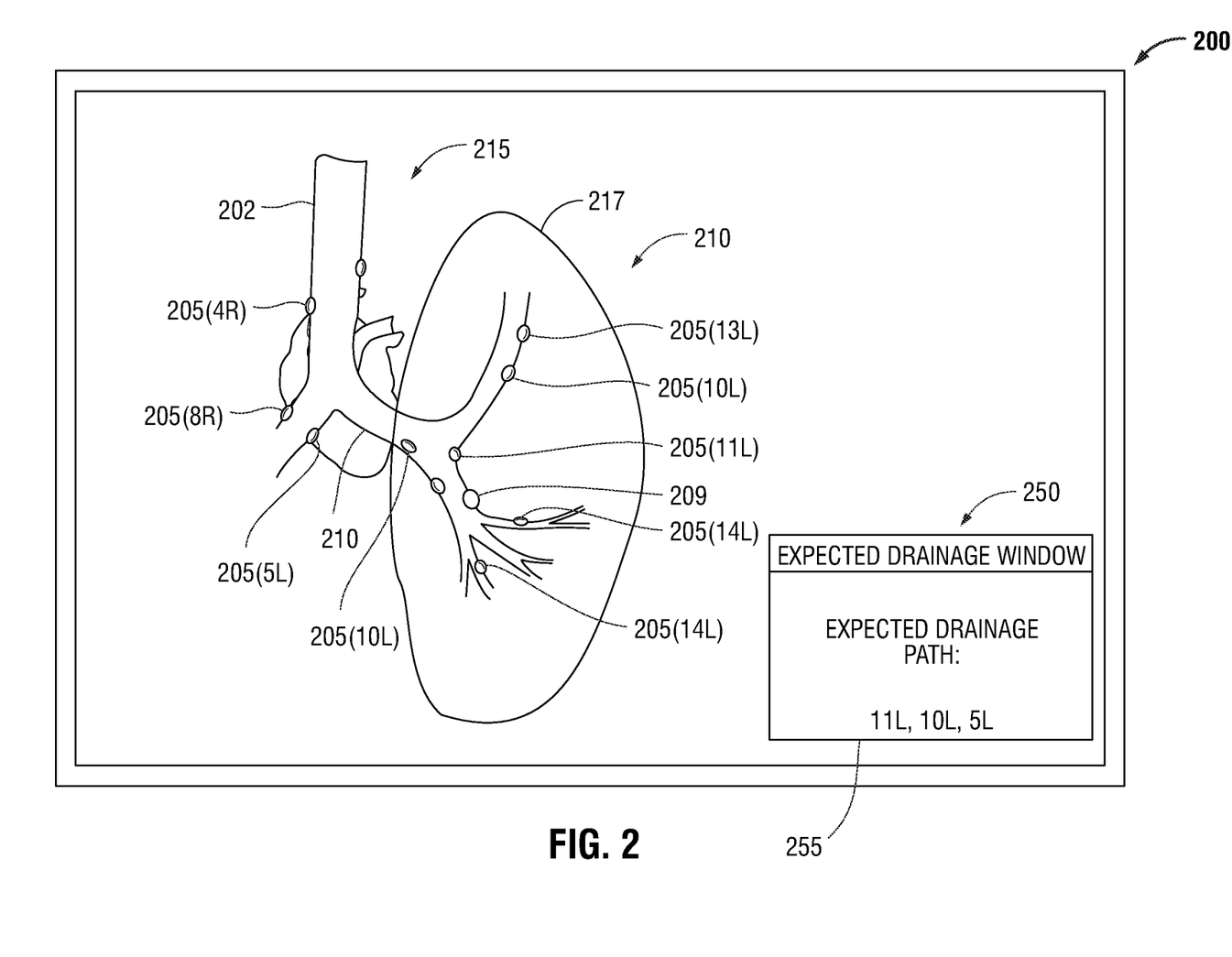
FIG. 2 illustrates a graphical user interface (GUI) utilized for displaying a 3D model of a lung including the locations of airways, lymph nodes, and regions of interest, in accordance with the present disclosure.

Referring now to FIG. 2, a user interface of the type that would be presented on display 81 is depicted, including a model window 200. Model window 200 includes a 3D model 215 of a lung and an expected drainage window 250. As shown in FIG. 2, 3D model 215 includes trachea 202, left lobe 217, containing airways 210, a plurality of lymph nodes 205 disposed on or around airways 210, and a region of interest 209. Region of interest 209 is illustrated as a non-uniform volume, which may include a tumor or other benign or non-benign volume that a clinician determines is important with regard to a laparoscopic procedure. Additionally, 3D model 215 may include lesions, markers, organs, and/or other physiological structures. Some or all of the aforementioned elements may be selectively displayed, such that the clinician may choose which elements should be displayed when viewing 3D model 215, and 3D model 215 may be viewed in various orientations. For example, if the clinician desires to view a particular section of the patient's lungs, the clinician may rotate and/or zoom in on the particular section of the patient's lungs.

Lymph nodes 205 are illustrated as oval-shaped swellings on airways 110. These may be manually identified by a clinician reviewing the CT images from which the 3D model is generated. This identification may be done as part of a CT image viewing stage in an application or alternatively from reviewing the 3D model itself. Further, there are systems of image processing known in the art through which the lymph nodes can be identified and depicted in the 3D model. These automatically detected lymph nodes may be subject to verification by the clinician upon review of the 3D model and either accepted or rejected based on the experience of the clinician.

Although shown in FIG. 2 as single lymph nodes, lymph nodes 205 may be clusters of multiple lymph nodes. Lung lymph nodes are assigned an "R" or an "L" for those lymph nodes located in the right lobe or left lobe, respectively, and are assigned a number based on location. For example, lymph nodes 12L correspond to pulmonary nodes in the lobar region, lymph nodes 11L correspond to pulmonary nodes in the interlobar region, and lymph nodes 10L correspond to pulmonary nodes in the hilar region, and each assignment may include multiple lymph nodes. As illustrated in FIG. 2, lymph nodes 205 include identifiers as to which of these regions they belong (e.g., 14L, 13L, 11L, 10L, 8R, and 4R).

As it relates to a region of interest 209, lymph nodes 205 may be separated into tiers, such as sentinel or primary lymph nodes, secondary lymph nodes, tertiary lymph nodes, etc. The lymphatic system drains from a sentinel lymph node to secondary lymph nodes to tertiary lymph nodes, etc. Sentinel lymph node are the first lymph nodes to which cancer cells are most likely to spread from a tumor. Generally, sentinel lymph nodes are those closest to a tumor, and along the expected drainage pathway. The drainage pathway extends next out to secondary nodes followed by tertiary nodes. The determination of which tier each of the plurality of nodes belongs to is based on, among other characteristics, the location of lymph nodes 205 with respect to region of interest 209 and the location of lymph nodes 205 with respect to the segments of the lung.

With respect to drainage pathways, an expected drainage pathway is depicted connecting lymph nodes 205 in FIG. 2, as shown in expected drainage window 250. Expected drainage window 250 may be displayed along with 3D model 215 within model window 200 or may pop out to be displayed separately. As shown in FIG. 2, expected drainage window 250 contains example lymph node information data 255 for an expected drainage pathway from region of interest 209. This expected drainage pathway may be based on the location of the region of interest 209, empirical evidence from prior analyses that is collected digitally and used to generate an algorithm that can predict the interconnectedness of lymph nodes through a combination of image processing, and comparative results collection and correlation. Alternatively, the expected drainage pathway may be based on the clinician's experience in conducting prior examination and may be identified by the clinician when conducting analyses or review of the CT images or 3D model. As depicted in FIG. 2, based on region of interest 209, the expected lymph node drainage pathway proceeds from region of interest 209 to pulmonary node 11L in the interlobar region (shown as 205(11L)) then to pulmonary node 10L in the hilar region (shown as 205(10L)) and to 5L, an aortic node located near the left subaortic valve. Additionally, based on the location of region of interest 209, lymph node 205(11L) is the expected sentinel node, lymph node 205(10L) is the expected secondary drain node, and lymph node 205(5L) is the expected tertiary drain node. If, for example, region of interest 209 was located in another location, the ordering of lymph nodes 205 may be different. Although only lymph node drainage to a third tier is illustrated, additional lymph nodes tiers may also be included in expected drainage window 250. It should be further noted that this may be just one drainage pathway to or from region of interest 209, and that multiple other drainage pathways may also exist for a particular region of interest and/or sentinel lymph node. Further, here the drainage pathway appears to be a pathway from regions closer to the trachea in the direction of the region of interest 209, and there may be further lymph nodes 205 along this drainage pathway more distal of region of interest 209.

In some embodiments, each tier of lymph nodes 205 may be displayed in 3D model 215 as a different color or different shading thereby allowing a clinician to visualize the likely drainage pathway. For example, sentinel nodes may be displayed in red, while secondary nodes are displayed in orange, and tertiary nodes are displayed in yellow. In this manner, a clinician may, by viewing 3D model 215, determine the likely lymph node drainage pathway without additional information. Although expected drainage window 250 details an expected drainage pathway, because each lymph node assignment, such as pulmonary node 11L, may include multiple lymph nodes it is necessary to determine an actual or confirmed lymph node drainage pathway, as described in the detailed description of FIG. 3.

Figure 3:
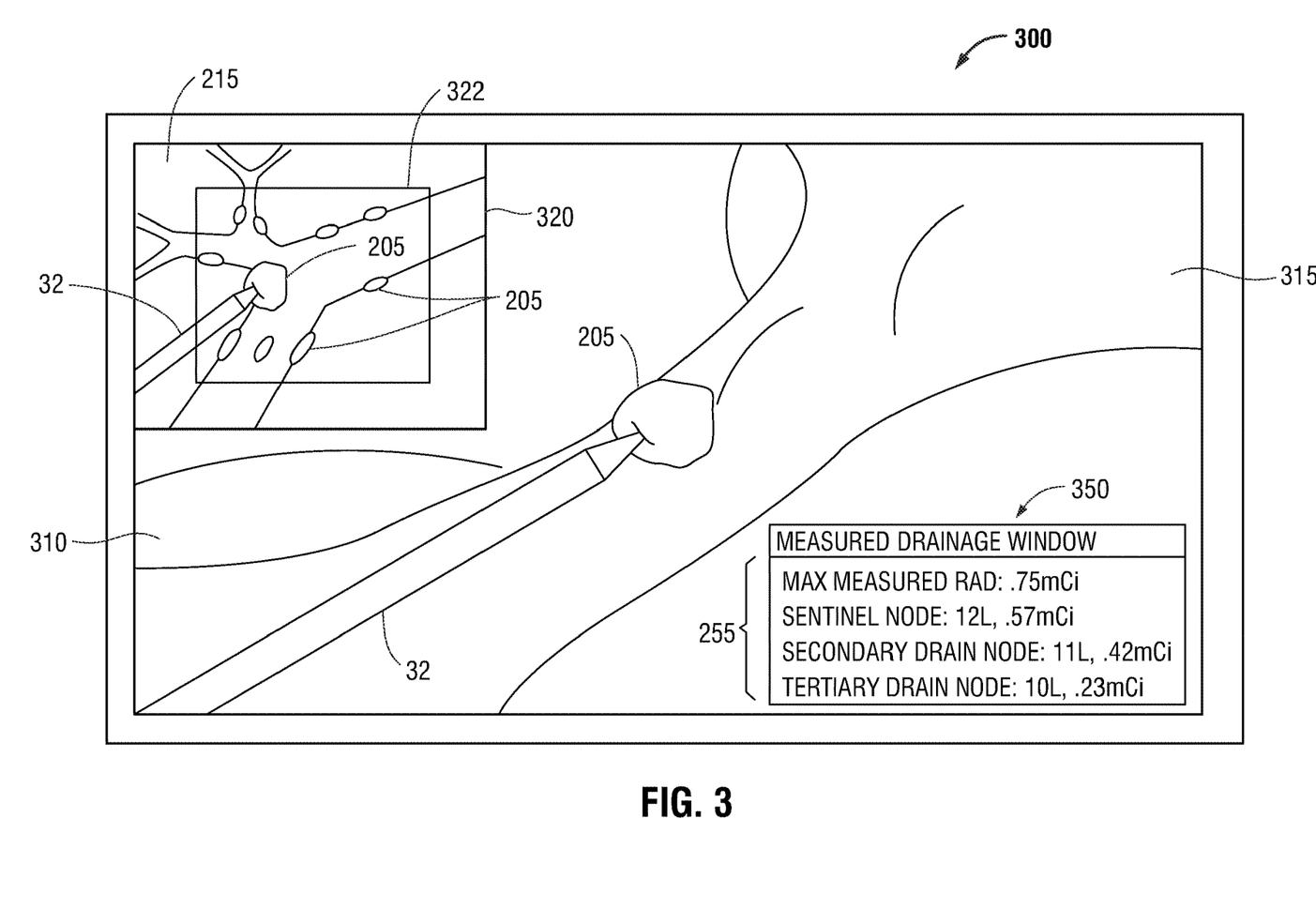
FIG. 3 illustrates a GUI utilized for visualizing lymph node specimen samples and determining accurate lymph node drainage pathways, in accordance with the present disclosure.

With reference now to FIG. 3, sampling window 300 is illustrated. In accordance with one aspect of the present disclosure, prior to collecting tissue samples, which may include biopsying and/or resecting a portion of lymph nodes 205 and/or region of interest 209, the region of interest 209 may be injected with a radioactive tracking agent (tracer) and/or a marking agent, such as an optical coloring agent or a dye, for example, by using surgical tool 32. Once the tracer has been injected into region of interest 209, the radiation emission levels throughout the lymphatic system in specific lymph nodes may be determined by non-invasively sampling likely lymph node drainage pathways. As an example, the clinician may utilize a radiological emissions detection tool (32 in FIG. 3) to obtain the radiation emission levels from a number of lymph nodes 205. Based on the differences in detected emissions, a more accurate lymph node drainage pathway may be determined.

In an alternative or additional aspect of the present disclosure, the lymph node drainage pathway may be determined using a marking agent (e.g., a dye). Once the marking agent has been injected into region of interest 209 using a surgical tool 32, tissue sampling (e.g., taking a biopsy of likely lymph nodes) may be undertaken and a determination made whether a particular sampled lymph node 205 includes the marking agent. If marking agent is found in a particular tissue sample, the drainage pathway can be mapped, thereby determining the lymph node drainage pathway.

Sampling window 300 displays a laparoscopic view 310 including a lymph node 205 from which a sample can be taken (either tissue or emissions) for determination of a lymph node drainage pathway, in accordance with the present disclosure. As shown in FIG. 3, sampling window 300 includes a location window 320, which includes a portion of 3D model 215 as a modeled representation corresponding to laparoscopic view 310. Location window 320 includes a bounding box 322 that serves to display the laparoscopic view 310 overlaid onto the 3D model. As can be readily appreciated, this provides greater context for the clinician when considering the laparoscopic view 310. Laparoscopic view 310 includes a real-time image of lymph node 205, tissue 315, and surgical tool 32, which is obtained by laparoscopic camera 35. In one embodiment, as a clinician manipulates the location of laparoscope 30 and the display shown in laparoscopic view 310 changes, the corresponding location within location window 320 and bounding box 322 changes the portion of the 3D model 215 which is depicted to ensure that the image within the bounding box 322 is presented properly in context with the 3D model. As noted above, a clinician may manually mark specific lymph nodes 205. This may be as a result of laparoscopic imaging via laparoscopic camera 35 providing greater clarity for uncovering lymph nodes 205 not seen in the models. In some embodiments, manual identification is the only mechanism available to identify a location of a lymph node 205 on the 3D model 215, and thus be represented in the images displayed in location window 320. The coordination between laparoscopic view 310 and location window 320 is due to the previous registration of 3D model 215 with the patient, which serves to align the laparoscopic images with the 3D model, so that locations of 3D model 215 corresponding to similar locations within the patient's airways within the EM field are consistently displayed. Thus, based on the location of laparoscope 30, which is trackable, the locations within 3D model 215 may be determined and updated, and data from 3D model 215, such as lymph node locations can be depicted in corresponding relationship with the laparoscopic view 310.

Further included within sampling window 300, is measured drainage window 350. Measured drainage window 350 includes lymph nodes information data 255 and is utilized to display a specific drainage pathway from region of interest 209, based on, for example, a tracking agent and/or a marking substance injected into region of interest 209. In the example depicted in measured drainage window 350 of FIG. 3, region of interest 209, previously injected with a tracer and was measured as having a radiation emission level of 0.75 millicurie (mCi). A 12L lymph node 205 was measured at 0.57 mCi, an 11L lymph node 205 was measured at 0.42 mCi, and a 10L lymph node 205 was measured at 0.28 mCi. Thus, from region of interest 209, the lymph node drainage pathway progresses from the 12L lymph node (sentinel node), through the 11L lymph node (secondary drain node), and to the 10L lymph node (tertiary drain node.)

Because each lymph node region (14L, 13L, 10L, etc.) contains multiple lymph nodes, each lymph node within a specific assignment may not drain from or to region of interest 209. By utilizing an emission detection process described herein, a more specific lymph node drainage pathway may be determined. This data can be incorporated into the 3D model data to effectively redraw the drainage pathway in instances where the expected drainage pathway proved inaccurate or incomplete.

As described in the detail description of FIG. 1, the physical location of surgical tool 32 may be tracked using EM sensors 94. Additionally, because 3D model 215 is registered with the patient's body, a clinician is able to confirm that the locations of lymph nodes 205, which are shown in 3D model 215, correspond with the physical location of EM sensor 94 of surgical tool 32. This assists to properly define the locations of the lymph nodes 205 for biopsy, resection, and/or analysis. As the clinician samples lymph nodes 205, based on the physical locations of surgical tool 32, measured drainage window 350 is updated with lymph node information data 255. Lymph node information data 255 may include the lymph node assignment and level of radiation levels or presence of marking agent. As a clinician continues to sample lymph nodes 205, 3D model 215 and location window 320 is continually updated to indicate the sampling of lymph nodes and measured drainage window 350 is continually updated to include additional lymph node information data 255, such as classification tier, lymph node assignment (12L, 10L, etc.) and radiation emission levels.

Figure 4:
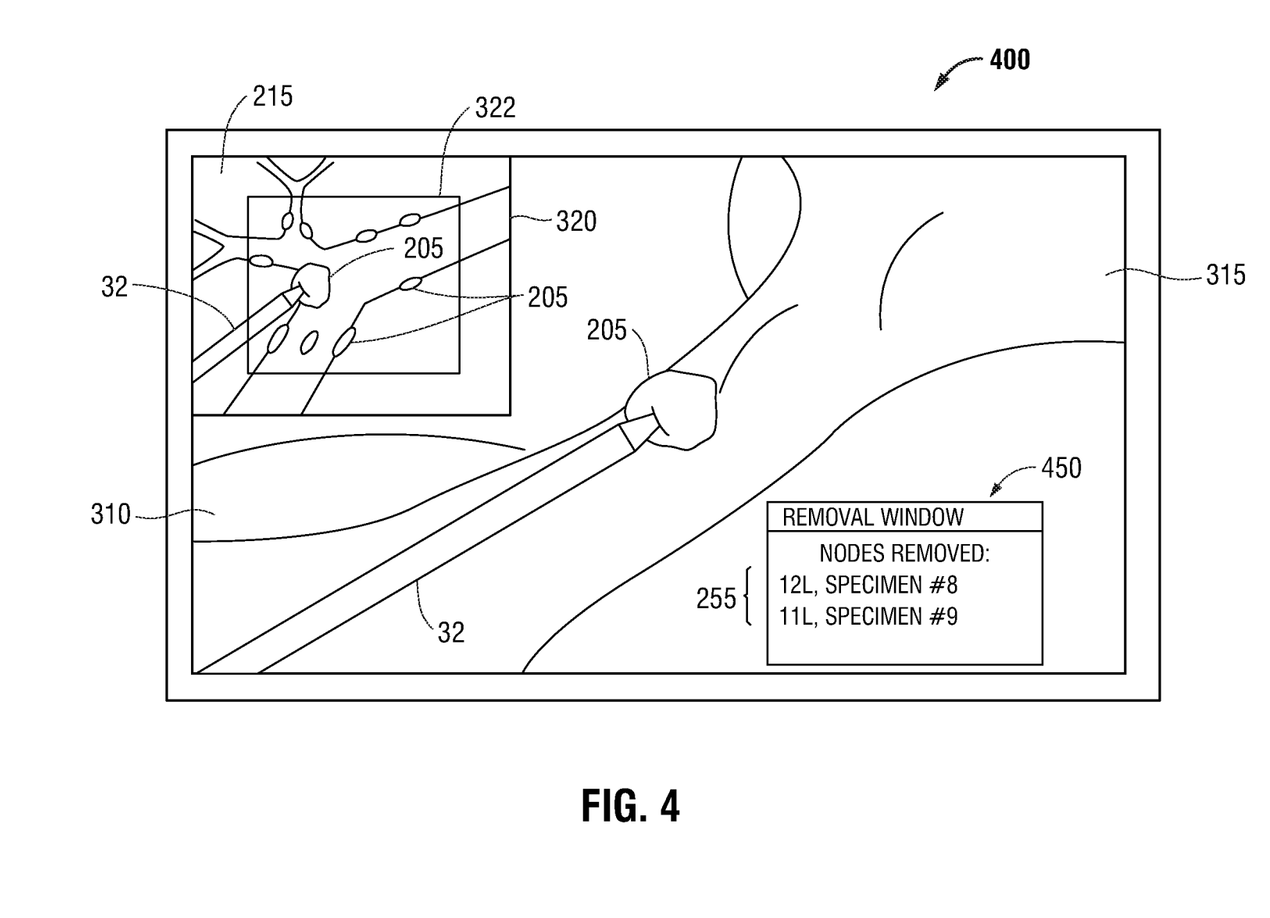
FIG. 4 illustrates a GUI utilized for visualizing lymph node specimens during a surgical procedure, in accordance with the present disclosure.

Referring now to FIG. 4, procedure window 400 is illustrated. Procedure window 400 is utilized in order to track, in real-time, resection and/or biopsy of lymph nodes 205 and/or region of interest 209. As shown in FIG. 4, procedure window 400 includes location window 320 and laparoscopic view 310. Similar to FIG. 3, location window 320 includes bounding box 322 that corresponds to the location within 3D model 215 that in turn corresponds to the location and images shown in laparoscopic view 310. Laparoscopic view 310 includes a display of surgical tool 32, lymph nodes 205, and tissue 315 and allows a clinician to see surgical tool 32 as it interacts with regions with the patient's body. As illustrated in FIG. 4, surgical tool 32 is shown as a biopsy tool in physical contact with lymph node 205.

Further included within procedure window 400 is removal window 450. Removal window 450 is utilized to determine which lymph nodes 205 and/or region of interest 209 have been biopsied and/or removed to provide a clinician with pertinent information regarding the lymph nodes 205 and/or region of interest 209. As the clinician biopsies and/or resects lymph nodes 205 and/or region of interest 209, based on the physical locations of EM sensor 94 of surgical tool 32, removal window 450 is updated with lymph node information data 255, which may include the lymph node assignment, lymph node specimen number, removal date, clinician name, and type of procedure performed on lymph node 205 and region of interest 209. For example, where a 12L lymph node 205 is removed, analyzed, or biopsied only, removal window 450 may be updated to include this information. During a procedure, as a clinician continues to biopsy, resect, and/or analyze lymph nodes 105, removal window 450 is continually updated. In addition, where the current procedure continues from a previous procedure, 3D model 215 from the previous procedure may be imported thereby updating the current 3D model 215 and importing within removal window 450 past dates, clinicians, and lymph nodes 205, which have already been analyzed or removed. Thus, procedure window 400 and removal window 450 allow a clinician to ensure that the correct lymph nodes are being removed and/or analyzed and ensures that previously removed and/or analyzed lymph nodes are handled appropriately.

Figure 5:
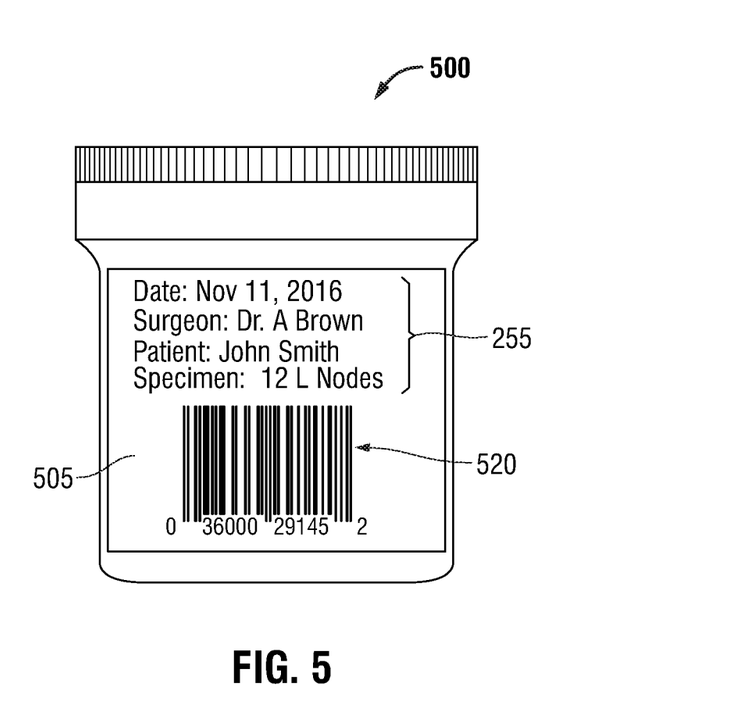
FIG. 5 illustrates a exemplary specimen container including a label of lymph node information in accordance with the present disclosure.

Referring now to FIG. 5, an illustration of a specimen container 500 containing a label 505, which includes lymph node information data 255 and barcode 520. Where necessary, a clinician is able to utilize information from measured drainage window 350 and removal window 450 and generate a printout of label 505 including lymph node information data 255. Label 505 may then be affixed to specimen container 500 thereby allowing the clinician to gain, among other benefits: (1) minimized labeling errors; and (2) confidence that the procedures performed on each lymph node 205 is known, as each label 505 will correspond to a single lymph node and include lymph node information data 255.

Figure 6:
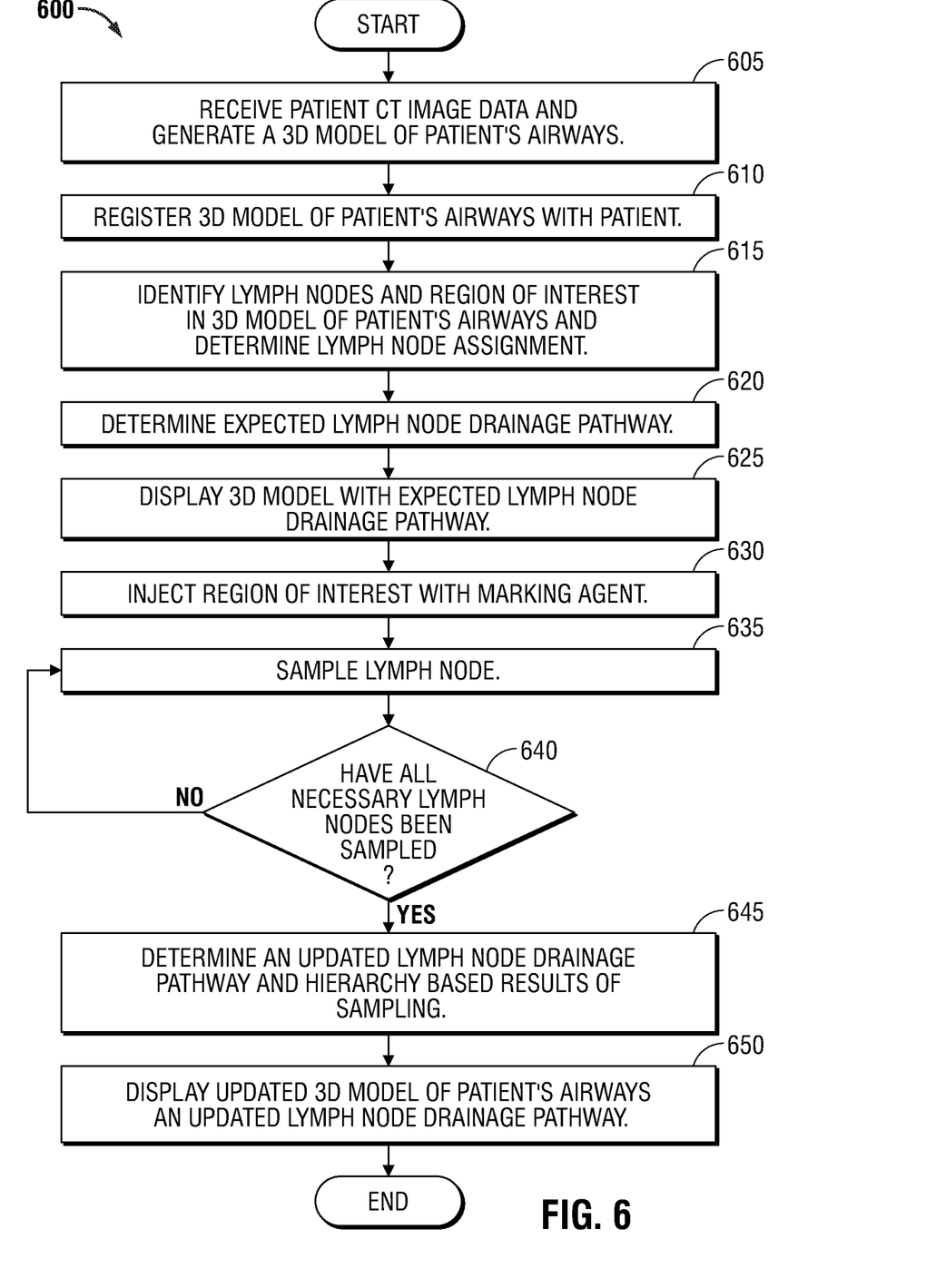
FIG. 6 illustrates a method for determining and displaying a lymph node drainage pathway in accordance with the present disclosures.

Referring now to FIG. 6, a flowchart illustrating a method 600 for determining and displaying a lymph node drainage pathway is shown in accordance with the present disclosure. Method 600 details steps taken prior to the removal of region of interest 209 and details both radiological and biopsy sampling. Generally, during the removal of lymph nodes 205, sentinel and possibly secondary lymph nodes 205 are removed. However, it is necessary to determine the locations of tertiary nodes for potential subsequent surgical procedures and confirmation of completion of removal. Method 600 begins at step 605 where patient CT image data is received and 3D model 215 is generated. As further described in the detailed description of FIG. 1, using CT images of the patient's airways, a 3D model, such as 3D model 215, may be generated from CT images using computing device 80. Next, at step 610, the locations within 3D model 215 are registered to corresponding physical locations of the patient's body.

Next, at step 615, one or more lymph nodes 205 and/or a region of interest 209 are identified within 3D model 215. The lymph node assignments (14L, 10L, 5L, etc.) are also identified within 3D model 215. Lymph nodes 205 and/or region of interest 209 are identified as described above from the CT images of the patient or the 3D model 215. Next, at step 620, based on the location of region of interest 209, expected drainage window 250 may be generated. As described in the detailed description of FIG. 2, lymph nodes 205 may be colored or shaded to allow a clinician to better determine where in 3D model 215 and the patient's body lymph nodes 205 are located. Next, at step 625, 3D model 215 is displayed along with the expected lymph node drainage pathway. Next, at step 630, region of interest 209 is injected with a marking agent, such as a tracer.

At step 635, a sample of lymph nodes 205 around region of interest 209 may be taken in order to determine lymph node drainage pathways, as described further in the detailed description of FIG. 3. Next, at step 640, a determination is made of whether all necessary lymph nodes have been sampled. If it is determined that all necessary lymph nodes 205 have been sampled, method 600 proceeds to step 645. If it determined, at step 640, that all necessary lymph nodes 205 have not been sampled method 600 returns to step 635.

At step 645, an updated lymph node drainage pathway is determined based on the sampling. Next, at step 650, the lymph node drainage pathway is updated and generated based on the samples and is displayed in measured drainage window 350. In some embodiments, each of lymph nodes 205 displayed within 3D model 215 as updated have different colors or shadings based on the lymph nodes drainage tier (sentinel, secondary, tertiary, etc.)

Figure 7:
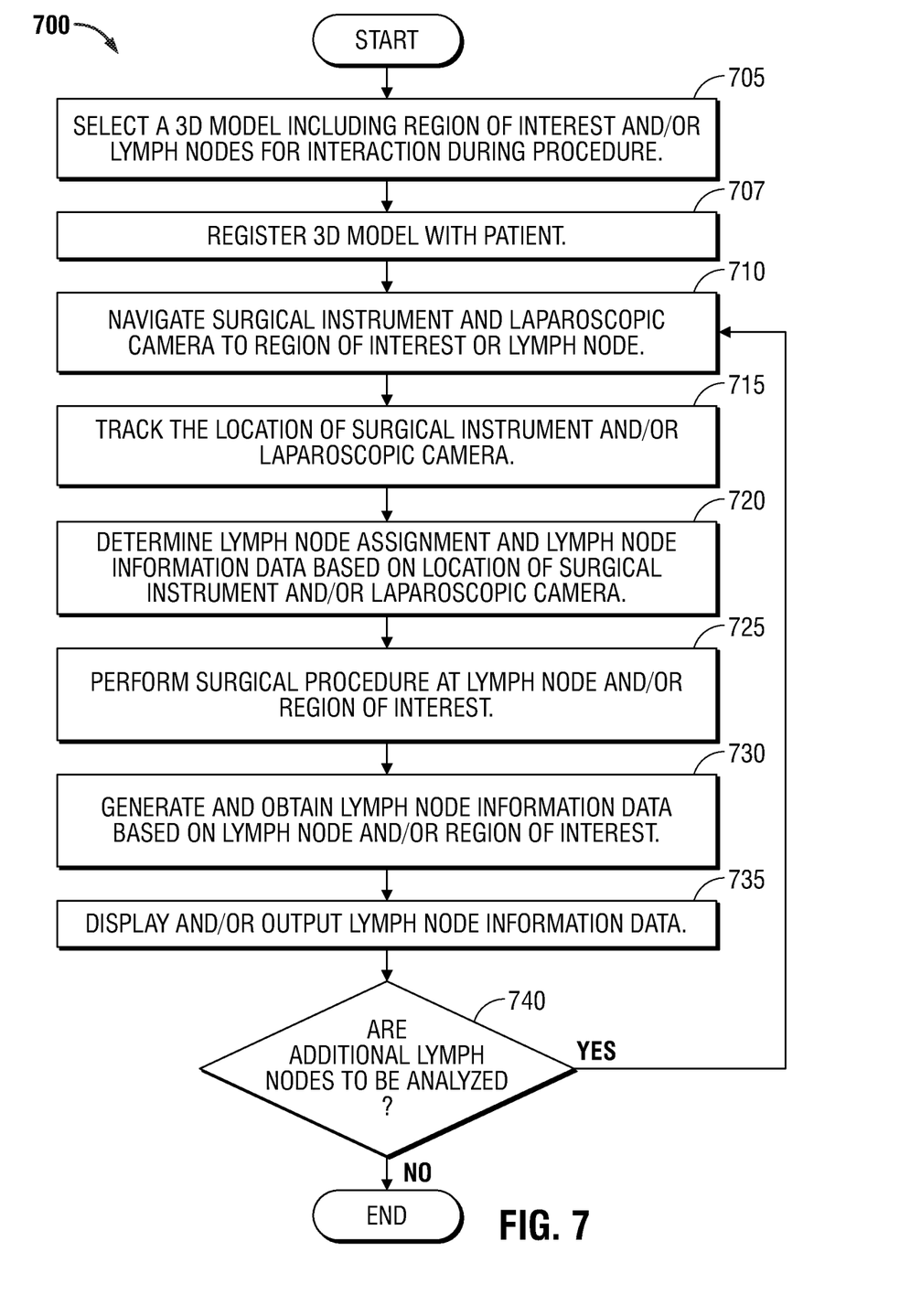
FIG. 7 illustrates a method for performing lymph node surgical procedures and presenting lymph node information data, in accordance with the present disclosures.

Turning now to FIG. 7, a flowchart illustrating an exemplary method 700 for performing lymph node surgical procedures and presenting lymph node information data 255 is shown, in accordance with the present disclosure. Method 700 details steps taken during removal of all or a portion of region of interest 209 and lymph nodes 205 and confirmation that accurate and correct lymph nodes 205 were removed. Method 700 begins at step 705 where a clinician selects a 3D model 215 including region of interest 209 or lymph node 205 for which a surgical procedure is to be performed. Next, at step 707, the selected 3D model is registered with the patient. Thereafter, at step 710, the clinician performs a laparoscopic procedure and moves surgical tool 32 and laparoscope 30 to region of interest 209 or lymph node 205, as further described in the detailed description of FIG. 1. As surgical tool 32 is moved to the physical location of lymph nodes 205 and/or region of interest 209, the location of EM sensor 94 of surgical tool 32 is tracked at step 715. Next, at step 720, using the physical location of laparoscope 30, laparoscopic view 310 changes. Location window 320 including images generated from 3D model 215 changes based on the physical location of EM sensor 94 of laparoscope 30 due to the registration between 3D model 215 and the patient and detection of EM sensor 94 in the EM field. Additionally, based on the location of EM sensor 94 of surgical tool 32 and or laparoscope camera 30, current and previous lymph node information data 255 of those lymph nodes 205 may be obtained. For example, where lymph nodes 205 have been previously biopsied, previous lymph node information data 255 may be obtained from computing device 80 and displayed.

Next, at step 725, a clinician may perform a biopsy, resection, and/or other surgical procedure with respect to lymph nodes 205 and/or region of interest 209. Next, at step 730, computing device 80 generates the lymph node information data 255, which may include a patient identification, lymph node name, specimen number, clinician name, procedure type, date of procedure, estimated volume of the target lymph node from preoperative imaging, relative mapping radiation, and/or image agent intensity. At step 735, lymph node information data 255 is displayed and continually updated via removal window 450 as surgical procedures are performed on lymph nodes 205 and/or region of interest 209, as further described in the detailed description of FIG. 4. Additionally, where necessary, the clinician has the option, at step 735, of outputting the lymph node information data 255 via a printout or a label such as label 510 of FIG. 5. Conversely, the information may be associated with a pre-labeled sample file, the pre-labeled file ID being scanned in coordination with placing the sample in the sample file.

Next, method 700 proceeds to step 740 where it is determined whether there are additional lymph nodes 205 and/or region of interest 209 which require a surgical procedure. If, at step 740, it is determined that no additional surgical procedures are required, method 700 ends. If, at step 740, it is determined that additional lymph nodes 205 and/or region of interest 209 require a procedure, method 700 returns to step 710, where surgical tool 32 and laparoscope camera 30 are navigated to another lymph node 205 or region of interest 209.

With specific reference to the methods described herein, though described in a particular order, the present disclosure is not intended to be so limited. For example, the registration step described with reference to both FIGS. 6 and 7 may occur at alternative times within the flow of the methods described without departing from the scope of the present disclosure. Further, the methods described here may be expressed in one or more applications, as described above, to produce one or more graphic user interfaces for presentation on a display in order to achieve the described methodology.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of lymphatic specimen tracking, visualization, and lymph node drainage pathway determination, the method comprising:
receiving computed tomographic (CT) image data corresponding to a CT scan;
generating a three-dimensional (3D) model of at least a portion of a patient's body based on the CT image data;
identifying one or more lymph nodes in the 3D model;
identifying a drainage tier of each lymph node of the one or more lymph nodes, the drainage tier including one of sentinel nodes, one or more secondary nodes, and one or more tertiary nodes;
performing a registration of the 3D model with one or more physical locations in the patient's body;
determining an expected lymph node drainage pathway away from a region of interest through the one or more lymph nodes;
displaying the 3D model and the expected lymph node drainage pathway;
tracking a location of a surgical instrument;
analyzing the one or more lymph nodes based on the tracked location of the surgical instrument;
measuring radiation emission levels from the region of interest; and
displaying a lymph node data user interface including:
an image of a first lymph node of the one or more lymph nodes at a previous tracked location of the surgical instrument and first lymph node information data including the radiation emission levels measured for the first lymph node; and
an image of a second lymph node of the one or more lymph nodes at a current tracked location of the surgical instrument and second lymph node information data including the radiation emission levels measured for the second lymph node, wherein the image of the first lymph node is displayed in a first color based on the identified drainage tier of the first lymph node and wherein the image of the second lymph node is displayed in a second color different from the first color based on the identified drainage tier of the second lymph node.

2. The method according to claim 1, further comprising:
injecting the region of interest with a marking agent;
sampling the one of more lymph nodes based on the expected lymph node drainage pathway; and
measuring the marking agent within the one or more lymph nodes.

3. The method according to claim 2, wherein the marking agent is selected from the group consisting of an optical coloring agent and a radioactive tracer.

4. The method according to claim 2, further comprising:
determining a measured lymph node drainage pathway away from the region of interest through the one or more lymph nodes based on the marking agent measured within the one or more lymph nodes; and
displaying the measured lymph node drainage pathway.

5. The method according to claim 4, wherein the marking agent is a radioactive agent and the displaying of the measured lymph node drainage pathway includes:
displaying measured emissions of the marking agent.

6. The method according to claim 2, wherein the lymph node data user interface includes one or more of a lymph node name, procedure type, patient information, date, marking agent measured, and clinician information.

7. A system for lymphatic specimen tracking and visualization, the system comprising:
a laparoscopic camera insertable into a patient and configured to obtain images;
a surgical tool insertable into the patient;
a camera sensor operatively associated with the laparoscopic camera;
a tool sensor operatively associated with the surgical tool;
an electromagnetic tracking system configured to track the camera sensor and the tool sensor;
one or more processors configured to execute instructions which, when executed, cause the one or more processors to:
receive computed tomographic (CT) image data corresponding to a CT scan;
generate a three-dimensional (3D) model of at least a portion of a patient's body from the CT image data;
identify one or more lymph nodes inside the 3D model;
identify a drainage tier of each lymph node of the one or more lymph nodes, the drainage tier including one of sentinel nodes, one or more secondary nodes, and one or more tertiary nodes;
perform a registration of the 3D model with one or more physical locations in the patient's body;
determine an expected lymph node drainage pathway away from a region of interest through the one or more lymph nodes;
track a location of the surgical tool;
analyze the one or more lymph nodes based on the tracked location of the surgical tool;
measure radiation emission levels from the region of interest;
cause a display to display a user interface including:
an image of a first lymph node of the one or more lymph nodes at a previous tracked location of the surgical tool and first lymph node information data including the radiation emission levels measured for the first lymph node; and
an image of a second lymph node of the one or more lymph nodes at a current tracked location of the surgical tool and second lymph node information data including the radiation emission levels measured for the second lymph node, wherein the image of the first lymph node is displayed in a first color based on the identified drainage tier of the first lymph node and wherein the image of the second lymph node is displayed in a second color different from the first color based on the identified drainage tier of the second lymph node.

8. The system according to claim 7, wherein the instructions, when executed, further cause the one or more processors to:
generate the user interface, the user interface including a sampling window configured to display the identified one or more lymph nodes and the surgical tool as it interacts with the identified one or more lymph nodes inside the patient's body.

9. The system according to claim 7, wherein the instructions, when executed, further cause the one or more processors to:
generate the user interface, the user interface including a measured drainage window configured to display the lymph node drainage pathway.

10. The system according to claim 7, wherein the instructions, when executed, further cause the one or more processors to:
generate the user interface, the user interface including a procedure window configured to display and track a surgical procedure being performed.

11. The system according to claim 7, wherein the instructions, when executed, further cause the one or more processors to:
receive a previous 3D model of at least a portion of the patient's body from a previous procedure including previous lymph node information data from the previous procedure; and
update the 3D model and the lymph node information data based on the previous 3D model and previous lymph node information data.

12. The system according to claim 7, wherein the instructions, when executed, further cause the one or more processors to:
generate the user interface, the user interface including a removal window configured to display and update the first and second lymph node information data during a surgical procedure.

13. The system according to claim 7, wherein the first and second lymph node information data include one or more of lymph node name, patient information, date, and clinician information.

14. The system according to claim 7, wherein the instructions, when executed, further cause the one or more processors to:
generate the user interface, the user interface including a location window configured to display a portion of the 3D model that corresponds with the images obtained by the laparoscopic camera.

15. A non-transitory computer readable storage medium, storing instructions, which when executed by a processor, cause the processor to:
receive computed tomographic (CT) image data corresponding to a CT scan;
generate a three-dimensional (3D) model of at least a portion of a patient's body from the CT image data;
output a display for identifying one or more lymph nodes inside the 3D model;
identify a drainage tier of each lymph node of the one or more lymph nodes, the drainage tier including one of sentinel nodes, one or more secondary nodes, and one or more tertiary nodes;
perform a registration of the 3D model with one or more physical locations in the patient's body;
determine an expected lymph node drainage pathway away from a region of interest through the one or more lymph nodes;
track a location of a surgical tool;
output a display for analyzing the one or more lymph nodes based on the tracked location of the surgical tool;
receive measured radiation emission levels corresponding to the region of interest;
generate a user interface including:
an image of a first lymph node of the one or more lymph nodes at a previous tracked location of the surgical tool and first lymph node information data including the radiation emission levels measured for the first lymph node; and
an image of a second lymph node of the one or more lymph nodes at a current tracked location of the surgical tool and second lymph node information data including the radiation emission levels measured for the second lymph node, wherein the image of the first lymph node is displayed in a first color based on the identified drainage tier of the first lymph node and wherein the image of the second lymph node is displayed in a second color different from the first color based on the identified drainage tier of the second lymph node.

16. The non-transitory computer readable storage medium according to claim 15, wherein the instructions, when executed, further cause the processor to:
generate the user interface, the user interface including a measured drainage window configured to display the lymph node drainage pathway.

17. The non-transitory computer readable storage medium according to claim 15, wherein the instructions, when executed, further cause the processor to:
generate the user interface, the user interface including a procedure window configured to display and track a surgical procedure being performed.

* * * * *